United States Patent [19]

Marissal et al.

[11] Patent Number: 4,684,522

[45] Date of Patent: Aug. 4, 1987

[54] SLENDERIZING AND ANTI-CELLULITIS COSMETIC COMPOSITION BASED ON AN EXTRACT OF A PLANT CONTAINING SAPONINS, AN EXTRACT OF ARNICA MONTANA L AND A KOLA NUT EXTRACT, AND TO A PROCESS FOR USING THE SAME

[75] Inventors: Jeanine Marissal, Monte Carlo, Monaco; Lucien P. Aubert, Cap D'Ail, France

[73] Assignee: Société Anonyme dite: BIOTHERM, Monaco, Monaco

[21] Appl. No.: 711,760

[22] Filed: Mar. 14, 1985

Related U.S. Application Data

[63] Continuation-in-part of Ser. No. 347,021, Feb. 8, 1982, abandoned.

[51] Int. Cl.$^4$ .............................................. A61K 35/78
[52] U.S. Cl. .................................................. 424/195.1
[58] Field of Search ...................................... 424/195.1

[56] References Cited

U.S. PATENT DOCUMENTS 3,914,416 10/1975 Gueyre et al. ........................ 514/63
4,187,291 2/1980 Marissal ............................ 242/195.1

FOREIGN PATENT DOCUMENTS 2296425 7/1976 France ............................... 424/195.1
2369840 2/1978 France ............................... 514/263

OTHER PUBLICATIONS

Potter's Cyclopaedia p. 18, 1950.
Lewis Medical Botany p. 213, col. 1, 1977.

*Primary Examiner*—Johnnie R. Brown
*Assistant Examiner*—John W. Rollins
*Attorney, Agent, or Firm*—Cushman, Darby & Cushman

[57] ABSTRACT

A cosmetic composition for application to the skin, having slenderizing and anti-cellulitis activity contains (i) an effective amount of a plant extract containing saponins, said extract being selected from the group consisting of *Hedera haelix* L extract, *Ruscus aculeatus* L extract and *Aesculus hipocastanus* L extract, said extract containing 30 to 100 percent saponins, (ii) an effective amount of an extract of Arnica Montana L, said extract being provided in the form of a tincture or a glycol extract, and (iii) an effective amount of kola nut extract, said extract containing caffeine in an amount ranging from 1.25 to 10 weight percent.

8 Claims, No Drawings

SLENDERIZING AND ANTI-CELLULITIS COSMETIC COMPOSITION BASED ON AN EXTRACT OF A PLANT CONTAINING SAPONINS, AN EXTRACT OF ARNICA MONTANA L AND A KOLA NUT EXTRACT, AND TO A PROCESS FOR USING THE SAME

This application is a continuation-in-part of application Ser. No. 347,021 filed Feb. 8, 1982, now abandoned.

The present invention relates to a cosmetic composition for application to the skin and, more particularly, to a composition possessing slenderizing and anti-cellulitis properties, as well as to a process for using said composition.

There has already been proposed in U.S. Pat. No. 4,187,291 a composition for combatting cellulitis and adipose swelling comprising in combination a non-hormonal in nature, organic iodine compound, a diffusion enzyme and a substance having anti-inflammatory and/or anti-edematous activity. This prior art composition exhibits good slenderizing activity, principally on women having an awkward or ungracious figure, especially in the areas of the pelvis and thighs. However, the results obtained using this prior art composition have only been perceptible after a relative long treatment period in the order of about 2 months.

Such a treatment, involving at least a daily massage over several weeks, is particularly tedious and costly, taking into account the nature of the active principles employed.

Indeed, women, after noticing only a small improvement after 2 to 3 weeks have a tendency to interrupt or space out the treatments which definitely influences and prolongs by as much the duration of the treatment.

It has now been observed that particularly significant results can be obtained in the treatment of cellulitis and fatty swelling in a much shorter time by using a cosmetic composition made in accordance with the present invention, which composition combines at least three active principles thus accomplishing a potentially beneficial activity.

It has been noted from tests carried out on a large sampling of women that an improvement of the figure in terms of the shape of the hips and the thighs could be obtained after a daily treatment of about 10 days and that a treatment on the order of 1 month was sufficient to obtan an average loss in terms of the shape of the hips and thighs on the order of 2 to 3.5 cm.

The cosmetic compositions according to the present invention provides then, relative to that of U.S. Pat. No. 4,187,291, the advantage of being more active and thus renders the treatment less tedious and less costly.

Thus, the present invention relates to, as a new industrial product, a cosmetic composition for application to the skin, said composition having a slenderizing and anti-cellulitis activity and containing in an appropriate cosmetic support or vehicle for application to the skin:

(i) an effective amount of at least one extract of a plant containing saponins, (ii) an effective amount of an extract of Arnica Montana L. (flowers of Arnica), and (iii) an effective amount of a kola nut extract.

Representative plants capable of providing extracts containing saponins include particularly extracts of *Hedera haelix* L. (or creeping ivy), of *Ruscus aculeatus* L. (or butcher's broom), of *Aesculus hipocastanus* L. (or horse-chestnut) and mixtures thereof.

According to the present invention the extracts of these plants contain from 30 to 100% of saponins and the extract is present in the composition of the present invention in an amount ranging from 0.5 to 8 percent by weight, expressed on a dry basis, relative to the total weight of the composition.

The *Hedera haelix* L. extract can result from a lixiviation extraction operation using water or by any other extraction process or it can even be obtained by other processes which remove certain common constituents such as proteins, lipids, carbohydrates, mucilages and tannins. Such an extraction process is principally described in French Pat. No. 73.21650 which discloses a process for preparing a flavonoidic and saponinic composition by the extraction of constituents from creeping ivy (*Hedera haelix* L.) in which the said ivy is freed from its alcohol soluble constituents other than flavonoidic and saponinic constituents, extracted with alcohol with the extraction alcohol then being evaporated.

The first stage of the process disclosed in this French patent consists in freeing from the ivy its alcohol constituents other than flavonoidic and saponinic constituents.

This stage is advantageously carried out by treating powdered or crushed ivy, for example, powdered or crushed wood of ivy and, advantageously ivy leaves, by a solvent in which the constituents of ivy other than the desired saponinic and flavonoidic constituents are soluble.

Among the solvents which are appropriate are principally, ketones, notably aliphatic ketones such as acetone, methyl ethyl ketone, etc., ethers, principally ethyl ether, aromatic hydrocarbons, such as benzene, saturated aliphatic hydrocarbons, advantageously halogenated, such as chlorinated derivatives of lower alkanes, for example, trichloroethylene.

This initial extraction is carried out in a solvent intended to free the alcohol soluble non-flavonoidic and non-saponinic constituents of ivy in a solid-liquid extractor by using from 2 to 2.5 liters of solvent per kilogram of the powdered or crushed ivy leaf or root. Interesting results are obtained by carrying out the extraction for several hours, for example, for 8 to 10 hours. The extraction is carried out by bringing the solvent to reflux.

Advantageously, this initial extraction is carried out using two successive solvents of a different nature.

The extraction is generally stopped when the extraction liquid becomes colorless.

The ivy powder which has been freed of its troublesome constituents is dried. A second stage of the process of this invention is then effected, this second stage being an alcoholic extraction of the flavonoidic and saponinic constituents which remain in the residue of the ivy powder.

This alcoholic extraction is carried out using alcohols, for example, methyl alcohol, ethyl alcohol or higher alcohol. It is advantageous to carry out this extraction stage in several successive steps by varying the nature and/or concentration of the alcohol employed in order to obtain an extraction, as complete as possible, of the active flavonoidic and saponinic principles.

This alcohol extraction is effected under conditions similar to those employed in the initial extraction. Thus, one usually employs from 2 to 2.5 liters of alcohol per kilogram of ivy powder remaining after the initial extraction for about 8 to 24 hours at the boiling point of the selected alcohol(s).

When several successive alcohol extractions have been carried out, the resulting alcoholic liquors are combined.

The third stage of the process disclosed in this French patent consists in evaporating to dryness the combined alcoholic extraction liquors.

This evaporation is carried out under reduced pressure at a temperature not exceeding 60° C. so as not to damage the active principles.

It is also possible in accordance with French Pat. No. 79.15415 to obtain an extract of creeping ivy (*Hedera haelix* L.) enriched to at least 50% of saponins.

In accordance with this process, initially an extraction using a lower alkanol having 1-4 carbon atoms of previously crushed ivy leaves, is effected. Preferably, methanol is employed. The alcohol is then evaporated by concentrating under vacuum the alcoholic liquors at the lowest possible temperature. Then the concentrate is dispersed, while stirring, in a mixture of water and a water immiscible organic solvent. The organic solvent can be, for instance, chlorinated hydrocarbons, ethers, ketones, esters and saturated or unsaturated cyclic hydrocarbons, optionally halogenated.

There is thus obtained a straw-colored yellow powder representing about one-tenth of the weight of the plant employed, said powder containing a minimum of 50% of saponins expressed as hederasaponin C.

Moreover, the titer of the extract can be increased up to 60% of saponins by a supplemental purification which consists in dissolving the extract obtained in the form of a powder in a lower alkanol, such as methanol, and precipitating the saponins by adding to the alcoholic solution an alkanol miscible organic solvent such as ethyl acetate, methylene chloride, ether or hexane. The precipitate formed is filtered and then dried.

The following example illustrates this process:

10 kg of dried and crushed ivy leaves are lixiviated with 75 liters of methanol. The methanolic liquors are then concentrated under a vacuum up to the production of 5 liters of concentrate.

The concentrate is then slowly poured, while stirring, into a 51/49 mixture of water/ethyl acetate. The lower aqueous phase is drawn off, washed with 3 liters of ethyl acetate, decanted, concentrated and dried.

908 g of a clear yellow powder titrating 51.8% of saponins, expressed as hederasaponin C, are thus produced.

The dry extract of *Ruscus aculeatus* L. (butcher's broom) used in accordance with the invention is obtained starting with previously crushed rhizomes which are extracted with a hydroalcoholic solution of an alcohol having 3-6 carbon atoms, preferably, n-butanol saturated with water. After evaporation of the butanolic phases, a residue is obtained that is taken up in an alcohol such as methyl alcohol, the saponins are precipitated with a mixture of ether and acetone. The saponins thus obtained are then taken up with water and extracted with ether. On evaporation of the aqueous phase, a crude extract is obtained. This process is more particularly described in French Pat. No. 69.23340 as well as in its Certificate of Addition No. 71.29817 which relates in particular to a process for purification of the crude saponin extract by passage through a nonionic resin column.

The extracts of *Ruscus aculeatus* L. obtained by these processes are provided in the form of a beige powder soluble at 2% in water and in alcohol at 60%. These extracts are essentially characterized by a saponins weight content greater than 65% and preferably between 70 and 80%.

The extract of *Aesculus hipocastanus* L. (horse chestnut) utilized in accordance with the invention can be a glycolic extract, a dry hydroalcoholic extract or even a fluid extract (U.S. Pharmacopeia) or a soft extract (U.S. Pharmacopeia).

Preferably, a soft extract prepared by lixiviation with alcohol at 60% tritrating 60% in saponins is employed. It is provided in the form of a very thick liquid having a caramel color and having a foam index between 8,500 and 10,500.

The Arnica Montana L. extract used in the compositions according to the present invention can be provided in the form of a tincture (U.S. pharmacopeia) or a glycol extract. Its concentration, expressed on a dry basis, can range from 0.01 to 0.5 percent relative to the total weight of the composition. Preferably, in accordance with the present invention, there is employed a glycol extract containing 2 to 5 percent by weight of said Arnica Montana L. extract on a dry basis and in this case the compositions of this invention contain about 0.5 to 10 percent by weight of this glycol extract.

The kola nut (Cola Nitida) extract can be provided in the form of a powder resulting from a hydroalcoholic extraction, or a fluid extract (U.S. Pharmacopeia) or a tincture (U.S. Pharmacopeia) or a wine of kola (U.S. Pharmacopeia). Preferably, there is employed a dry hydro methanolic or ethanolic extract and in this case the concentration of this extract can very between 0.2 and 2 weight percent.

The kola nut extract must, preferably, have a caffeine content between 1.25 and 10 percent.

According to the invention a dry hydroalcoholic extract, such as defined above and containing about 10 percent caffeine, is preferred.

The composition according to the invention can additionally contain other active principles capable of assisting the slenderizing and anti-cellulitis activity.

Representative other active principles include, particularly, water soluble organic compounds derived from monomethyl trisilanol, such as for example, monomethyl trisilanol mannuronate sold commercially by Exymol under the tradename "Algisium" (aqueous solution containing 1% of monomethyl trisilanol mannuronate) or the lactate derivative, sold by the same company under the tradename of "Lasilium" (aqueous solution containing 1% of monomethyl trisilanol lactate).

According to the present invention these organic compounds are present, preferably, in the compositions of the invention in an amount between 2 and 20% as a 1% solution thereof or between 0.02 and 0.2% by weight, expressed as active material.

The compositions according to the present invention can be provided in various forms and principally in the form of an emulsion, a cream, a milk, a gel, an aerosol foam or the like.

In addition to the active principles, these compositions can also contain other conventional components for this type of composition, such as for example, perfumes, dyes, preservatives and the like.

The present invention also relates to a process for combatting cellulitis and fatty swelling, this process comprising applying to the parts of the body to be treated by a massaging action a sufficient amount of the composition of the present invention.

Generally, the duration of the treatment is variable but it produces very satisfactory results when it is carried out for a period between about 10 days and 1 month with the slenderizing composition of this invention being applied daily.

The following non-limiting examples illustrate the composition of the present invention.

Unless otherwise stated, all parts and percentages are by weight.

EXAMPLE 1

In accordance with the present invention, a slenderizing cream is prepared by admixing the following components:
Isopropyl myristate: 3.0 g
Turnsole oil: 6.0 g
Triple pressed stearic acid: 4.0 g
Cetyl alcohol: 4.0 g
Glycerol monostearate: 4.0 g
Triethanolamine: (99%) 0.8 g
Methyl p-hydroxybenzoate: 0.1 g
Propyl p-hydroxybenzoate: 0.2 g
Soft extract of horsechestnut (U.S. Pharmacopeia): 2.0 g
Glycol extract containing 2.5 weight percent of Arnica Montana L extract on a dry basis: 5.0 g
Hydroethanol extract of kolanut (dry matter): 0.5 g
Perfume: 0.5 g
Sterile demineralized water, sufficient amount for: 100 g This cream when applied daily on the hips and thighs for a treatment period of about 15 days satisfactorily reduces cellulitis and the adipose swelling of the hips and thighs.

EXAMPLE 2

In accordance with the present invention a slenderizing cream is prepared by admixing the following components:
lIsopropyl myristate: 4.2 g
Petrolatum oil: 4.0 g
Triple pressed stearic acid: 3.0 g
Cetyl alcohol: 1.5 g
Glycerol stearate: 3.0 g
Triethanolamine: (99%) 0.8 g
Methyl p-hydroxybenzoate: 0.1 g
Propyl p-hydroxybenzoate: 0.2 g
Monomethyl trisilanol mannuronate (1% solution in water): 10.0 g
n-butanol extract of *Ruscus aculeatus* L (dry matter): 2.0 g
Methanol extract of *Hedera haelix* L (dry matter): 1.0 g
Glycol extract containing 2.5 weight percent of Arnica Montana L extract on a dry basis: 5.0 g
Hydroethanol extract of kola nut (dry matter): 1.0 g
Perfume: 0.3 g
Sterile demineralized water, sufficient amount for: 100 g Daily application of this composition on the hips and thighs for a treatment period in the order of 2 to 3 weeks provides a satisfactory reduction of cellulitis and the adipose swelling of the hips and thighs.

EXAMPLE 3

In accordance with the present invention, a slenderizing and anti-cellulitis gel is prepared by admixing the following components:
Polyacrylic acid (Carbopol 940): 0.4 g
Triethanolamine (99%): 0.4 g
Propylene glycol: 8.0 g
Methyl p-hydroxybenzoate: 0.1 g
Propyl p-hydroxybenzoate: 0.2 g
Monomethyl trisilanol mannuronate (1% solution in water): 10.0 g
n-butanol extract of *Ruscus aculeatus* L (dry matter): 0.5 g
Methanol extract of *Hedera haelix* L (dry matter): 0.5 g
Glycol extract containing 2.5 weight percent of Arnica Montana L extract on a dry basis: 2.0 g
Hydroethanol extract of kola nut (dry matter): 0.5 g
Perfume: 0.3 g
Sterile demineralized water, sufficient amount for: 100 g This gel when applied daily to the hips and to the thighs provides, after a treatment of about 10 to 15 days, an average loss of about 2 to 3 cm.

EXAMPLE 4

A slenderizing milk is prepared by admixing the following components:
Petrolatum oil: 16 g
Isopropyl palmitate: 2 g
Liquid lanolin: 1 g
Triple pressed stearic acid: 2.5 g
Glycerol stearate: 2.5 g
Triethanolamine (99%): 0.8 g
Propylene glycol: 2 g
Methyl p-hydroxybenzoate: 0.2 g
Propyl p-hydroxybenzoate: 0.1 g
Monomethyl trisilanol mannuronate (1% solution in water): 5.0 g
n-butanol extract of *Ruscus aculeatus* L (dry matter): 0.7 g
Methanol extract of *Hedera haelix* L (dry matter): 0.7 g
Glycol extract containing 2.5 weight percent of Arnica Montana L extract on a dry basis: 2.0 g
Hydroethanol extract of kola nut (dry matter): 0.7 g
Perfume: 0.3 g
Sterile demineralized water, amount sufficient for: 100 g.

What is claimed is:

1. A cosmetic composition for application to the skin, said composition having slenderizing and anti-cellulitis activity and containing:
   (i) an effective amount of a plant extract containing saponins, said extract being selected from the group consisting of
   (a) an extract of the leaves of *Hedera haelix* L obtained (1) from a lixiviation extraction with water, or (2) from an extraction operation consisting in extracting undesirable products with a solvent selected from the group consisting of an aliphatic ketone, an ether, an aromatic hydrocarbon and a chlorinated lower alkane, followed by an extraction with an alcohol, or (3) from an alcohol extraction follows by concentration of the resulting extract and dispersion of the resulitng concentrated extract in a mixture of water and a water immiscible organic solvent and concentration of the water phase;

(b) an extract of rhizomes of *Ruscus aculeatus* L obtained from a hydroalcoholic extraction wherein the alchol has 3-6 carbon atoms, followed by evaporation of the extract, taking up the residue in methanol, precipitating the saponins with a mixture of ehter and acetone, taking up the precipitate with water an extracting the water solution with ether;

(c) an extract of *Aesculus hipocastanus* L, said extract being a glycolic extract, a dry hydroalcoholic extract, or a fluid or soft extract according to U.S. Pharmacopeia; and (d) a mixture containing two or more of (a), (b) and (c), said extracts (a), (b) and (c) containing from 30 to 100 percent sponins, (ii) an effective amount of an extract of the flowers of Arnica Montana L, said extract being obtained as a tincture according to U.S. Pharmacopeia or as a glycol extract; and (iii) an effective amount of an extract of kola nut obtained (1) as a hydroalcoholic extract or (2) as a fluid extract, a tincture or a wine of kola according to U.S. Pharmacopeia, said extract of kola nut containing caffeine in an amount ranging from 1.25 to 10 weight percent.

2. The composition of claim 1 wherein said extract of a plant containing saponins is present in an amount ranging from 0.5 to 8 percent by weight, expressed on a dry basis, relative to the total weight of said composition.

3. The composition of claim 1 which also contains from 0.02 to 0.20 weight percent, expressed as active material, of a monomethyl trisilanol derivative selected from the group consisting of monomethyl trisilanol mannuronate and monomethyl trisilanol tactate.

4. The composition of claim 1 wherein said extract of Arnica Montana L is present in an amount ranging from 0.01 to 0.5 percent, expressed on a dry basis, relative to the total weight of said composition.

5. The composition of claim 1 wherein said extract of Arnica Montana L is a glycol extract containing from 2 to 5 percent by weight of said Arnica Montana L on a dry basis, said glycol extract being present in said composition in an amount ranging from 0.5 to 10 percent relative to the total weight of said composition.

6. The composition of claim 1 wherein said kola nut extract is a dry hydroalcoholic extract and is present in an amount ranging from 0.2 to 2 percent relative to the total weight of said composition.

7. A cosmetic composition for application to the skin, said composition having selnderizing and anti-cellulitis activity and containing:

(i) from 0.5 to 8 percent by weight, expressed on a dry basis of a plant extract containing saponins, said extract being selected from the group consisting of (a) an extract of the leaves of *Hedera haelix* L obtained (1) from a lixiviation extraction with water, or (2) from an extraction operation consisting in extrascting undesirable products with a solvent selected from the group consisting of an aliphatic ketone, an ether, an aromatic hydrocarbon and a chlorinated lower alkane, followed by an extraction with an alcohol, or (3) from an alcohol extraction followed by concentration of the resulting extract and dispersion of the resulting concentrated extract in a mixture of water and a water immiscible organic solvent and concentration of the water phase;

(b) an extract of rhizomes of *Ruscus alculeatus* L obtained from a hydroalcoholic extraction wherein the alcohol has 3-6 carbon atoms, followed by evaporation of the extract, taking up the residue in methanol, precipitating the saponins with a mixture of ether and acetone, taking up the precipitae with water and extracting the water solution with ether;

(c) an extract of *Aesculus hipocastanus* L, said extract being a glycolic extract, a dry hydro-alcoholic extract, or a fluid or soft extract according to U.S. Pharmacopeia; and (d) a mixture containing two or more of (a), (b) and (c), said extracts (a), (b) and (c) containing from 30 to 100 percent saponins, (ii) from 0.5 to 10 percent by weight of a glycol extract of the flowers of Arnica Montana L, said glycol extract containing from 2 to 5 percent by weight of said Arnica Montana L and (iii) from 0.2 to 2 percent by weight of a dry hydroalcoholic extract of kola nut.

8. A process for combatting cellulitis and fatty swelling of a person suffering from cellulitis and fatty swelling comprising a pplying to the part of the body to be treated by a massaging action for a period of time ranging from about ten days to one month, an effective amount of a composition containing (a) an extract of the leaves of *Hedera haelix* L obtained (1) from a lixiviation extraction with water, or (2) from an extraction operation consisting in extracting undesirable products with a solvent selected from the group consisting of an aliphatic ketone, an ether, an aromatic hydrocarbon and a chlorinated lower alkane, followed by an extraction with an alcohol, or (3) from an alcohol extraction followed by concentation of the resulting extract and dispersion of the resulting concentrated extract in a mixture of water and a water immiscible organic solvent and concentration of the water phase;

(b) an extract of rhizomes of *Ruscus aculeatus* L obtained from a hydroalcoholic extraction wherein the alcohol has 3-6 carbon atoms, followed by evaporation of the extract, taking up the residue in methanol, precipitating the sponins with a mixture of ether and acetone, taking up the precipitate with water and extracting the water solution with ether;

(c) an extract of *Aesculus hipocastanus* L, said extract being a glycolic extract, a dry hydroalcoholic extract, a or a fluid or soft extract according to U.S. Pharmacopeia; and (d) a mixture containing two or more of (a), (b) and (c), said extracts (a), (b) and (c) containing from 30 to 100 percent saponins, (ii) an effective amount of an extract of the flowers of Arnica Montana L, said extract being obtained as a tincture according to U.S. Pharmacopeia or as a glycol extract; and (iii) an effective amount of an extract of kola nut obtained (1) as a hydroalcoholic extract or (2) as a fluid extract, a tincture or a wine of kola according to U.S. Pharmacopeia, said extract of kola nut containing caffeine in an amount ranging from 1.25 to 10 wieght percent.

* * * * *

UNITED STATES PATENT AND TRADEMARK OFFICE
CERTIFICATE OF CORRECTION

PATENT NO.   :   4,684,522

DATED        :   August 4, 1987

INVENTOR(S)  :   Marissal et al.

It is certified that error appears in the above-identified patent and that said Letters Patent is hereby corrected as shown below:

In The Heading

[30]   Foreign Application Priority Date

February 10, 1981   France   81.02571

Signed and Sealed this

Twelfth Day of July, 1988

Attest:

DONALD J. QUIGG

Attesting Officer　　　　Commissioner of Patents and Trademarks